(12) United States Patent
Pageard

(10) Patent No.: US 10,682,170 B2
(45) Date of Patent: Jun. 16, 2020

(54) MULTIFUNCTIONAL ABLATION DEVICE

(71) Applicant: Medtronic CryoCath LP, Toronto (CA)

(72) Inventor: Jean-Luc Pageard, Montreal (CA)

(73) Assignee: Medtronic CryoCath LP, Toronto, Ontario ( * ) Notice: Subject to any disclaimer, the term of this patent is extended or adjusted under 35 U.S.C. 154(b) by 692 days.

(21) Appl. No.: 15/001,699

(22) Filed: Jan. 20, 2016

(65) Prior Publication Data

US 2016/0166306 A1    Jun. 16, 2016

Related U.S. Application Data

(63) Continuation of application No. 12/696,233, filed on Jan. 29, 2010, now Pat. No. 9,445,859.

(51) Int. Cl.
*A61B 18/02* (2006.01)
*A61B 90/00* (2016.01)
(Continued)

(52) U.S. Cl.
CPC .......... *A61B 18/02* (2013.01); *A61B 18/1492* (2013.01); *A61B 90/39* (2016.02); *A61B 2018/0022* (2013.01); *A61B 2018/00023* (2013.01); *A61B 2018/00041* (2013.01); *A61B 2018/00214* (2013.01); *A61B 2018/00255* (2013.01); *A61B 2018/00285* (2013.01); *A61B 2018/00351* (2013.01); *A61B 2018/00357* (2013.01); *A61B 2018/00375* (2013.01);
(Continued)

(58) Field of Classification Search
CPC ............ A61B 18/02; A61B 2018/0212; A61B 2018/0262; A61B 2018/0022; A61B 2018/0025; A61B 2018/00261
USPC ...................................... 606/20–26
See application file for complete search history.

(56) References Cited

U.S. PATENT DOCUMENTS

| 5,261,411 A | 11/1993 | Hughes |
| 5,542,928 A | 8/1996 | Evans et al. |

(Continued)

FOREIGN PATENT DOCUMENTS

| WO | 9901074 A1 | 1/1999 |
| WO | 0200128 A2 | 1/2002 |

(Continued)

OTHER PUBLICATIONS

Propylene Dow et al., A Guide to Clycols, Dec. 31, 2003, consisting of 58 pages.
(Continued)

*Primary Examiner* — Ronald Hupczey, Jr.
(74) *Attorney, Agent, or Firm* — Christopher & Weisberg, P.A.

(57) ABSTRACT

An intravascular catheter is provided, including a flexible elongate body; an expandable element positioned on the elongate body; a substantially linear thermal segment located proximally of the expandable element, the thermal segment defining a first flexibility, where the thermal segment is positioned between two portions of the catheter body each including a flexibility less than that of the thermal segment; a first fluid flow path in fluid communication with the expandable element; and a second fluid flow path in fluid communication with the thermal segment.

14 Claims, 4 Drawing Sheets

(51) Int. Cl.
*A61B 18/14* (2006.01)
*A61B 18/00* (2006.01)

(52) U.S. Cl.
CPC ............... *A61B 2018/00577* (2013.01); *A61B 2018/00994* (2013.01); *A61B 2018/0212* (2013.01); *A61B 2018/0262* (2013.01)

(56) References Cited

U.S. PATENT DOCUMENTS

| | | | |
|---|---|---|---|
| 5,788,647 A | 8/1998 | Eggers | |
| 5,899,897 A | 5/1999 | Rabin et al. | |
| 5,938,660 A | 8/1999 | Swartz et al. | |
| 6,012,457 A | 1/2000 | Lesh | |
| 6,119,041 A | 9/2000 | Pomeranz et al. | |
| 6,132,397 A | 10/2000 | Davis et al. | |
| 6,164,283 A | 12/2000 | Lesh | |
| 6,235,019 B1 | 5/2001 | Lehmann et al. | |
| 6,270,493 B1 | 8/2001 | Lalonde et al. | |
| 6,283,959 B1* | 9/2001 | Lalonde | A61B 18/02 606/21 |
| 6,355,029 B1 | 3/2002 | Joye et al. | |
| 6,379,348 B1 | 4/2002 | Onik | |
| 6,416,511 B1 | 7/2002 | Lesh et al. | |
| 6,428,534 B1 | 8/2002 | Joye et al. | |
| 6,527,769 B2 | 3/2003 | Langberg et al. | |
| 6,537,271 B1 | 3/2003 | Murray et al. | |
| 6,551,274 B2* | 4/2003 | Heiner | A61B 18/02 604/102.02 |
| 6,620,131 B2 | 9/2003 | Pham et al. | |
| 6,666,858 B2* | 12/2003 | Lafontaine | A61B 18/02 604/95.04 |
| 6,913,604 B2* | 7/2005 | Mihalik | A61B 18/02 606/20 |
| 7,001,378 B2 | 2/2006 | Yon et al. | |
| 7,101,368 B2 | 9/2006 | Lafontaine | |
| 7,527,622 B2 | 5/2009 | Lane et al. | |
| 7,853,331 B2 | 12/2010 | Kaplan et al. | |
| 8,123,741 B2 | 2/2012 | Marrouche et al. | |
| 2002/0045894 A1 | 4/2002 | Joye et al. | |
| 2003/0125721 A1* | 7/2003 | Yon | A61B 18/02 606/21 |
| 2006/0004351 A1* | 1/2006 | Arless | A61B 18/02 606/21 |
| 2009/0112239 A1 | 4/2009 | To | |

FOREIGN PATENT DOCUMENTS

| | | |
|---|---|---|
| WO | 0200128 A3 | 1/2002 |
| WO | 03020334 A2 | 3/2003 |
| WO | 2006124176 A1 | 11/2006 |

OTHER PUBLICATIONS

International Search Report and Written Opinion dated Apr. 8, 2011, for corresponding International Application No. PCT/CA2011/000064; International Filing Date: Jan. 21, 2011 consisting of 8-pages.

Supplementary European Search Report dated Nov. 17, 2016 for corresponding European Application No. EP 11 73 6556; consisting of 9 pages.

European Patent Office, Communication pursuant to Article 94(3) EPC, dated Oct. 24, 2019, for corresponding EP Application No. 11 736 557.7, 7 pages.

* cited by examiner

MULTIFUNCTIONAL ABLATION DEVICE

CROSS-REFERENCE TO RELATED APPLICATION

This application is a continuation of patent application Ser. No. 12/696,233, filed Jan. 29, 2010, entitled MULTIFUNCTIONAL ABLATION DEVICE, the entirety of which is incorporated herein by reference.

STATEMENT REGARDING FEDERALLY SPONSORED RESEARCH OR DEVELOPMENT n/a

TECHNICAL FIELD

The present invention relates to a method and system for thermal tissue treatment, and in particular, towards systems and methods of use thereof for treating multiple tissue sites having varying geometries.

BACKGROUND

Minimally invasive devices, such as catheters, are often employed for surgical procedure, including those involving ablation, dilation, and the like. In a particular situation, an ablation procedure may involve creating a series of interconnecting lesions in order to electrically isolate tissue believed to be the source of an arrhythmia. During the course of such a procedure, a physician may employ several different catheters having variations in the geometry and/or dimensions of the ablative element in order to produce the desired ablation pattern. Each catheter may have a unique geometry for creating a specific lesion pattern, with the multiple catheters being sequentially removed and replaced to create the desired multiple lesions. Exchanging these various catheters during a procedure can cause inaccuracies or movement in the placement and location of the distal tip with respect to the tissue to be ablated, and may further add to the time required to perform the desired treatment. These potential inaccuracies and extended duration of the particular procedure increase the risk to the patient undergoing treatment. Accordingly, it would be desirable to provide a single medical device having the ability to provide ablative patterns of various shapes, without the need for additional catheters or the like having a single geometric orientation, and thus, limited in the ability to provide multiple ablative patterns.

SUMMARY

The present invention advantageously provides a medical system having the ability to provide ablative patterns of various shapes to treat different targeted tissue sites while maintaining a substantially static position of the medical device. In particular, a medical device is provided, having an elongate catheter body; a first treatment region on the catheter body; a second treatment region proximal to the first treatment region, where the second treatment region defines a first deflection profile and is disposed between two adjacent catheter body segments defining deflection profiles different from the first deflection profile, and a third treatment region located distally of the first treatment region. The first treatment region may include an expandable element and the second treatment region can include a substantially linear thermal segment. The first treatment region may be operable independently from the second treatment region. The device may further include a first fluid flow path in fluid communication with the first treatment region, a second fluid flow path in fluid communication with the second treatment region, and a cryogenic fluid source in fluid communication with at least one of the first and second fluid flow paths. Radiopaque markers may be positioned at a boundary between the second treatment region and one of the adjacent catheter body segments.

An intravascular catheter is also provided, including a flexible elongate body; an expandable element positioned on the elongate body; a substantially linear thermal segment located proximally of the expandable element, the thermal segment including a flexibility or deformational capacity, where the thermal segment is positioned between two adjacent portions of the catheter body each including a flexibility or deformational capacity different from the thermal segment (for example, the adjacent portions having a rigidity greater than a rigidity of the thermal segment); a first fluid flow path in fluid communication with the expandable element; and a second fluid flow path in fluid communication with the thermal segment. The first fluid flow path may be operable independently from the second fluid flow path. The first fluid flow path may include a first fluid injection lumen, the second fluid flow path may include a second fluid injection lumen; and the first fluid flow path and the second fluid flow path can include a common exhaust lumen.

A method of treating cardiac tissue is also provided, including positioning an expandable element of a medical device proximate a pulmonary vein; positioning a substantially linear thermal segment of the medical device proximate an atrial wall, the thermal segment being more flexible than medical device segments adjacent to the thermal segment; applying a deflective force from a proximal portion of the medical device to the thermal segment, the deflective force causing the thermal segment to deflect towards the atrial wall; and ablating at least one of the pulmonary vein and the atrial wall with the medical device. Positioning the expandable element can include expanding the expandable element in the pulmonary vein to substantially occlude the pulmonary vein; applying a deflective force can include applying an axial force in a distal direction along a longitudinal axis of the medical device; and ablating at least one of the pulmonary vein and the atrial wall can include circulating a cryogenic fluid through at least one of the expandable element and the thermal segment.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
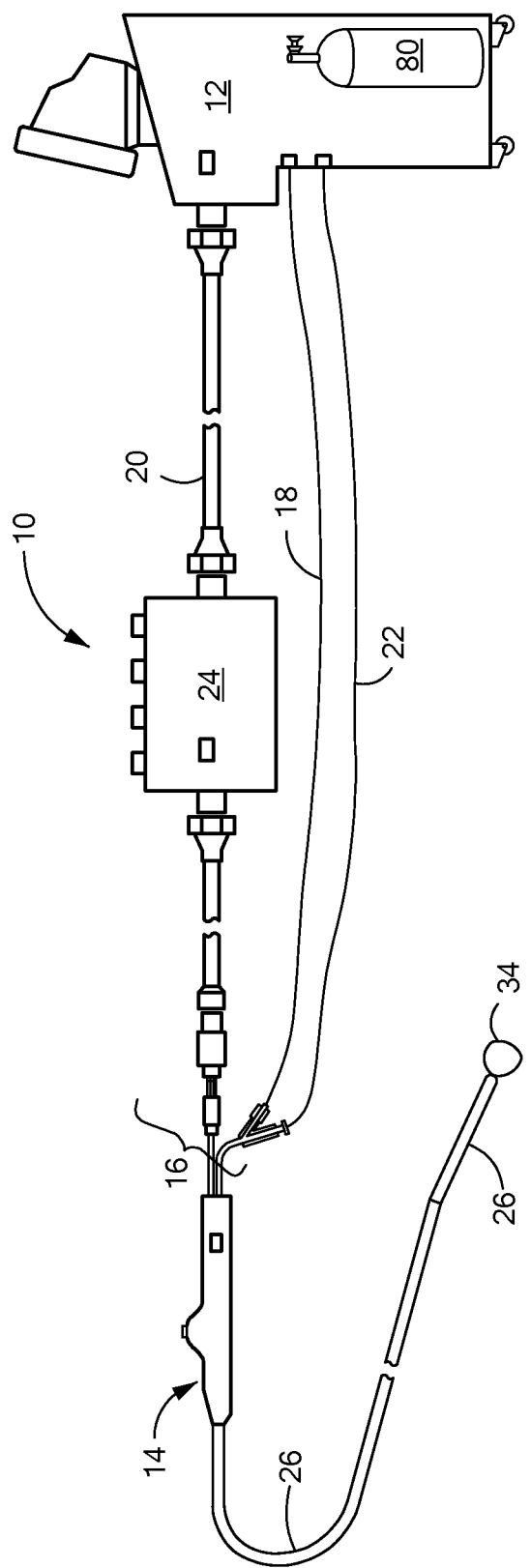
FIG. 1 is an illustration of an embodiment of a medical system constructed in accordance with the principles of the present invention.

The present invention advantageously provides a medical system having the ability to provide ablative patterns of various shapes to treat different targeted tissue sites while maintaining a substantially static position of the medical device. Referring now to the drawing figures in which like reference designations refer to like elements, an embodiment of a medical system constructed in accordance with principles of the present invention is shown in FIG. 1 and generally designated as "10." The system generally includes a cooling unit or console 12 coupled to a medical device 14 through an umbilical system 16. The medical device 14 may be a medical probe, a catheter, a balloon-catheter, as well as other devices deliverable or otherwise positionable through the vasculature and/or proximate to a tissue region for treatment. In particular, the medical device 14 may include a device operable to thermally treat a selected tissue site, including cardiac tissue. The medical system 10 may also include one or more sensors to monitor the operating parameters throughout the system, including for example, pressure, temperature, flow rates, volume, or the like in the console 12, the umbilical system 16, and/or the medical device 14.

Umbilical system 16 may include three separate umbilicals: a coaxial cable umbilical 18, an electrical umbilical 20 and a vacuum umbilical 22. Although separate umbilicals are shown, it is contemplated that one or more connections may be included in one or more umbilicals having one or more coaxial or otherwise integrally contained passages or conduits therethrough providing electrical and fluid communication between the medical device 14 and the console 12. An outer vacuum umbilical may be suitable for a medical device having multiple layers or balloons. If the user wishes to perform a radiofrequency ("RF") ablation procedure, radiofrequency energy can be provided to electrodes on the medical device 14 via electrical umbilical 20 to perform an RF ablation technique. Electrical umbilical 20 can include an electrocardiograph ("ECG") box 24 to facilitate a connection from one or more electrodes on the medical device 14 to an ECG monitor (not shown). Coaxial umbilical 18 may include both a cooling injection umbilical and a vacuum umbilical that provide respective inlet and return paths for a refrigerant or coolant used to cool a tissue-treating section of the device 14. The vacuum umbilical 22 may provide a safety conduit allowing excess coolant or gas to escape from the device 14 if the pressure within the medical device 14 exceeds a predefined limit. The vacuum umbilical 22 can also be used to capture air through a leak of the outer vacuum system where it is outside the patient and as a lumen to ingress blood when inside the patient.

Figure 2:
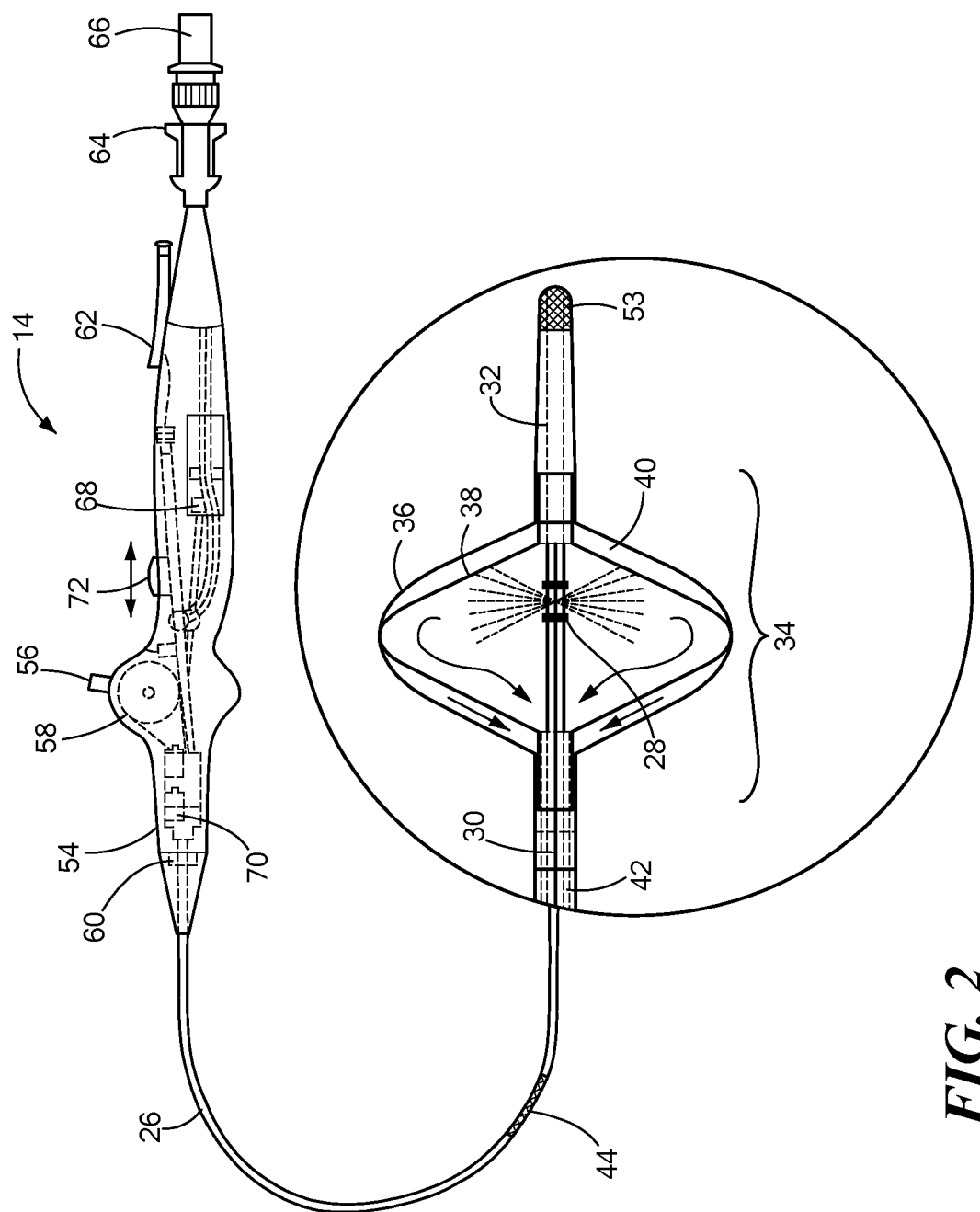
FIG. 2 is an illustration of an embodiment of a medical device constructed in accordance with the principles of the present invention.

Now referring to FIG. 2, the medical device 14 is shown in more detail. The medical device 10 may include an elongate body 26 passable through a patient's vasculature. The elongate body 26 may define a proximal portion and a distal portion, and may further include one or more lumens may disposed within the elongate body 26 thereby providing mechanical, electrical, and/or fluid communication between the proximal portion of the elongate body 26 and the distal portion of the elongate body 26. For example, the elongate body 26 may include an injection lumen 28 and an exhaust lumen 30 defining a fluid flow path therethrough. In addition, the elongate body 26 may include a guidewire lumen 32 movably disposed within and/or extending along at least a portion of the length of the elongate body 26 for over-the-wire applications. The guidewire lumen 32 may define a proximal end and a distal end, and the guidewire lumen 32 may be movably disposed within the elongate body 26 such that the distal end of the guidewire lumen 32 extends beyond and out of the distal portion of the elongate body 26.

The medical device may include one or more treatment regions for energetic or other therapeutic interaction between the medical device 14 and a treatment site. The treatment regions may deliver, for example, radiofrequency energy, cryogenic therapy, or the like. For example, the device 14 may include a first treatment region 34 having a thermal treatment element, such as an expandable membrane or balloon and/or one or more electrodes or other thermally-transmissive components, at least partially disposed on the elongate catheter body. In a particular example, the first treatment region 34 may include a first expandable/inflatable element or balloon 36 defining a proximal end coupled to the distal portion of the elongate body 26 of the medical device 14, while further defining a distal end coupled to the distal end of the guidewire lumen 32. As such, due to the movable nature of the guidewire lumen 32 about the elongate body 26, any axial and/or longitudinal movement of the guidewire lumen 32 may act to tension or loosen the first expandable element 36, i.e., extend or retract the expandable element 36 from a lengthened state to a shortened state during an inflation or deflation thereof. In addition, the first expandable element 36 may have any of a myriad of shapes, and may further include one or more material layers providing for puncture resistance, radiopacity, or the like. The first expandable element 36 may be in communication with the fluid injection and exhaust lumens of the medical device 14 as described above.

The medical device 14 may further include a second expandable/inflatable element or balloon 38 contained within or otherwise encompassed by the first expandable element 36 such that an interstitial region, envelope or space 40 is defined therebetween. The second expandable element 38 may be in communication with the fluid injection and exhaust lumens of the medical device 14 as described above, i.e., a fluid flow path may provide an inflation fluid or coolant, such as a cryogenic fluid or the like, to the interior of the second expandable element 38. Further, the interstitial region 40 may be in fluid communication with an interstitial lumen 42 providing a fluid flow path or avenue separate and independent from a fluid flow path delivering fluid or otherwise in communication with an interior of the second expandable element 38. The second pathway provides an alternate exhaust route for fluid that may leak from the interior of the second expandable element 38 into the interstitial region 40 or fluid entering the medical device 14 from the exterior. In particular, the isolation of the interstitial lumen 42 from the interior of the second expandable element 38 provides an alternate route for fluid to circulate in the case of a rupture or leak of either the first or second expandable elements, as well as allowing for the injection or circulation of fluids within the interstitial region 40 independently of fluids directed towards the second expandable element 38. Towards that end, the interstitial region may be in fluid communication with a fluid source, a vacuum source, or the like separate from a fluid source, vacuum source or otherwise in fluid communication with the interior of the second expandable element 38. Alternatively, the interstitial lumen 42 may be joined to or otherwise in fluid communication with the injection lumen 28 and the interior of the second expandable element 38 to provide a single exhaust or vacuum source for the medical device 14.

Figure 3:
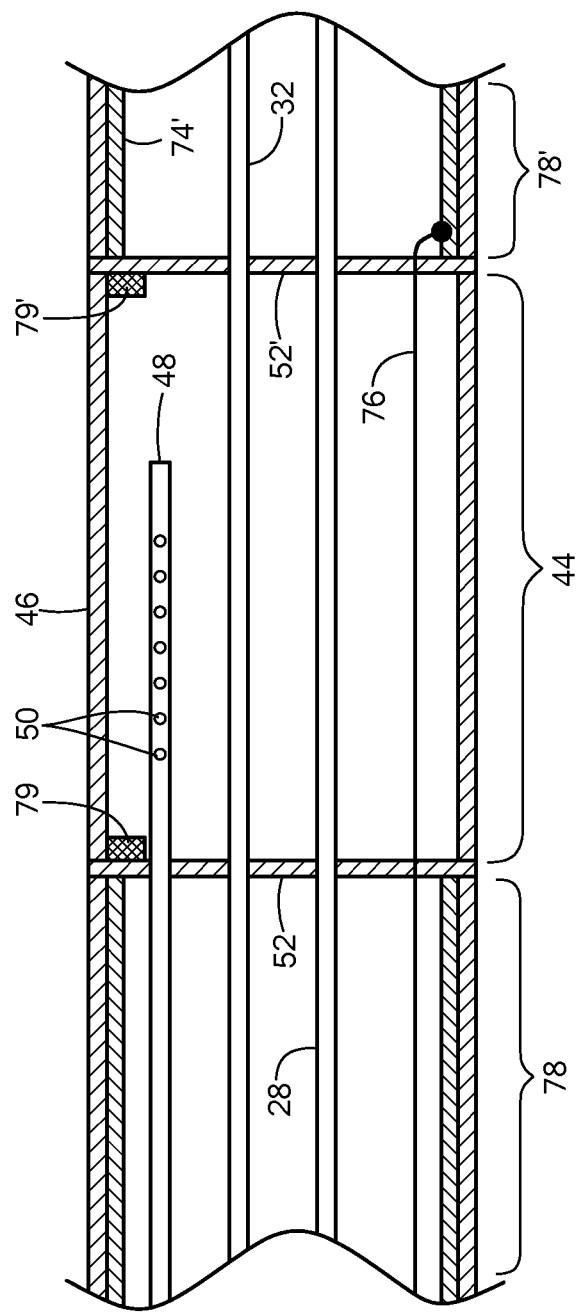
FIG. 3 is an additional illustration of the medical device shown in FIG. 2.

Now referring to FIG. 3, the medical device may further include a second treatment region 44 located proximally of the first treatment region 34, where the second treatment region 44 is operable independently and separately from the first treatment region 34. For example, the second treatment region 44 may be fluidically isolated or sealed from fluid flow with the first treatment region 34. The first and second treatment regions 34, 44 may generally provide the ability to deliver therapeutic treatment to a plurality of locations while maintaining the medical device 14 in a substantially fixed or static position.

The two treatment regions may also provide the ability to provide treatment or therapeutic energy to varying locations having different dimensions, shapes, or other geometric and anatomical characteristics. As described above, the first treatment region 34 may include one or more expandable elements or balloons. The first treatment region 34 may thus provide for arcuate, circular, and/or circumferential treatment patterns. In turn, the second treatment region 44 may include a substantially linear, elongate thermal segment 46 enabling energetic or thermal exchange with a contacted tissue area. Of note, the thermal segment 46 may be substantially linear when not experiencing any external loading or force, but may retain sufficient flexibility to curve into an arcuate, curvilinear shape to contact a desired tissue region. The thermal segment may be constructed from one or more materials imparting thermally conductive properties, such as nylon, polyethylene terephthalate ("PET"), and/or polyethylene ("PE") for example. In particular, the thermal segment 46 may provide sufficient thermal conductivity for ablation of contacted tissue through the use of a cryogenic refrigerant or a radiofrequency or other heat source coupled to or otherwise in thermal communication with the thermal segment 46.

Such thermal communication may be achieved, for example, by a fluid flow path in fluid communication with the thermal segment 46 that is independently operated or otherwise separated from a fluid flow path delivering a cooling or treatment medium to the first treatment region 34. For example, a secondary fluid injection lumen 48 may be in fluid communication with an interior of the thermal segment 46 of the second treatment region 44. The secondary fluid injection lumen 48 may include one or more apertures 50 therein for dispersing, expanding, or otherwise delivering a fluid to the thermal segment 46. The secondary fluid injection lumen 48 may be placed in fluid communication with a fluid supply common to the first treatment region 34, or may be coupled to a separate and independently operated fluid source. Where a common fluid source is elected, one or more valves, controllers, or the like may provide for the controlled, independent, and separate dispersion or circulation of fluid through the two injection lumens. Such valves, controllers, or the like may be located in a portion of the medical device 14 and/or in the console 12.

The thermal segment 46 may further include sealed transverse sections or walls 52, 52' spanning from the outer walls or layers of the elongate body 26 and around the one or more lumens extending towards the distal portion of the medical device that restrict or wholly prevent fluid dispersed within the thermal segment 46 from travelling distally towards the first treatment region 34. The thermal segment 46 may further include a secondary exhaust lumen (not shown), or the exhaust lumen 30 may be in fluid communication with the second treatment region 44, thereby allowing a single exhaust or vacuum source to remove expended coolant from both the first and second treatment regions jointly.

Continuing to refer to FIG. 3, the medical device may further include a third treatment region 53 located distally of the first treatment region 34, where the third treatment region 53 is operable independently and separately from the first and second treatment regions 34, 44 through one or more independently operated and/or isolated fluid lumens (not shown). For example, the third treatment region 53 may be fluidically isolated or sealed from fluid flow with the first and second treatment region. The plurality of treatment regions 34, 44, 53 may generally provide the ability to deliver therapeutic treatment to a plurality of locations while maintaining the medical device 14 in a substantially fixed or static position. In particular, the third treatment region 53 may provide for a "spot" ablation of discrete tissue locations, while also providing for anchoring of the distal end of the medical device 14 through cryoadhesion with contacted tissue. The third treatment region 53 may be constructed from one or more metals, thermally conductive polymers, and/or composites thereof.

The medical device 14 may further include one or more temperature and/or pressure sensors (not shown) proximate the treatment region(s) for monitoring, recording or otherwise conveying measurements of conditions within the medical device 14 or the ambient environment at the distal portion of the medical device 14. The sensor(s) may be in communication with the console 12 for initiating or triggering one or more alerts or therapeutic delivery modifications during operation of the medical device 14.

Referring to FIGS. 2 and 3, the medical device 14 may include a handle 54 coupled to the proximal portion of the elongate body 26, where the handle 54 may include an element such as a lever or knob 56 for manipulating the catheter body and/or additional components of the medical device 14. For example, a pull wire 58 with a proximal end and a distal end may have its distal end anchored to the elongate body 26 at or near the distal end. The proximal end of the pull wire 58 may be anchored to an element such as a cam in communication with and responsive to the lever 56.

The handle 54 can further include circuitry for identification and/or use in controlling of the medical device 14 or another component of the system. For example, the handle may include one or more pressure sensors 60 to monitor the fluid pressure within the medical device 14. Additionally, the handle may be provided with a fitting 62 for receiving a guidewire that may be passed into the guidewire lumen 32.

The handle 54 may also include connectors that are matable directly to a fluid supply/exhaust and control unit or indirectly by way of one or more umbilicals. For example, the handle may be provided with a first connector 64 that is matable with the co-axial fluid umbilical 18 and a second connector 66 that is matable with the electrical umbilical 20. The handle 54 may further include blood detection circuitry 68 in fluid and/or optical communication with the injection, exhaust and/or interstitial lumens. The handle 54 may also include a pressure relief valve 70 in fluid communication with the injection, exhaust and/or interstitial lumens to automatically open under a predetermined threshold value in the event that value is exceeded.

Continuing to refer to FIGS. 2-3, the medical device 14 may include an actuator element 72 that is movably coupled to the proximal portion of the elongate body 26 and/or the handle 54. The actuator element 72 may further be coupled to the proximal portion of the guidewire lumen 32 such that manipulating the actuator element 72 in a longitudinal direction causes the guidewire lumen 32 to slide towards either of the proximal or distal portions of the elongate body 26. As a portion of either and/or both the first and second expandable elements 36,38 may be coupled to the guidewire lumen 32, manipulation of the actuator element 72 may further cause the expandable element(s) to be tensioned or loosened, depending on the direction of movement of the actuator element 72, and thus, the guidewire lumen 32. Accordingly, the actuator element 72 may be used to provide tension on the expandable element(s) 36,38 during a particular duration of use of the medical device 14, such as during a deflation sequence, for example. The actuator element 72 may include a thumb-slide, a push-button, a rotating lever, or other mechanical structure for providing a movable coupling to the elongate body 26, the handle 54, and/or the guidewire lumen 32. Moreover, the actuator element 72 may be movably coupled to the handle 54 such that the actuator element 72 is movable into individual, distinct positions, and is able to be releasably secured in any one of the distinct positions.

Referring again to FIG. 3, the second treatment region 44 may be deflectable, steerable, or otherwise manipulated into a desired position or configuration independently or differently from the first treatment region 34 and/or adjacent portions of the elongate body 26. In particular, the elongate body 26 of the medical device 14 may be constructed from one or more layers 74, 74' of material or differing components to provide a desired degree of flexibility while maintaining the capability to transmit torque along the length of the medical device 14. The layers 74, 74' may include a multitude of polymers, plastics, and composites thereof, as well as braided or other structural reinforcing materials/components running therethrough. The elongate body 26 may further include one or more steering wires 76 or actuation mechanisms to deliver a force to a particular segment or portion of the medical device 14, such as a region proximate to the second treatment region 44, in addition to the pull wire 58 described above, which may provide deflection or steering of the first treatment region 34. The construction of the elongate body 26 substantially dictates its resulting deflection or bending behavior when a force is applied, i.e., its deflection profile.

The second treatment region 44 may define a deflection profile different from a deflection profile or behavior of adjacent sections 78, 78' of the catheter body 26. For example, the thermal segment 46 of the second treatment region 44 may have a construction different from the adjacent sections 78, 78' of the catheter body 26, resulting in a different flexibility, deflection or bending result when a force is applied. The different construction may include different use or multitudes of select materials, as well as using selected materials in a different order or relationship to one another. In a particular example, the second treatment region 44 may have greater flexibility than the adjacent section 78, 78'. The thermal segment 46 may have a width or thickness of material less than a width of material constituting portions of the catheter body 26. In addition and/or as an alternative, the thermal segment 46 may be devoid of or have reduced structural reinforcing components (such as braided constructs, longitudinal splines, deflection biasing members, or the like) compared to portions of the catheter body 26. The variations in deflection behavior between the second treatment region 44 and the surrounding portions of the catheter body 26 may allow the second treatment region 44 to be deflected or bent towards a targeted tissue for treatment while the medical device 14 remains substantially static or in place. In addition, the variations in bending or deflection behavior between the second treatment region 44 and the surrounding catheter body segments may allow for the transmission of a deflective force from a catheter body section to the second treatment region 44, as described in more detail below. In addition, one or more radiopaque markers 79, 79' may be positioned at a boundary between the second treatment region 44 and either of the adjacent catheter body sections or segments 78, 78' to facilitate positioning of the treatment region through known medical imaging methodologies.

In an exemplary system, a fluid supply 80 including a coolant, cryogenic refrigerant, or the like, an exhaust or scavenging system (not shown) for recovering or venting expended fluid for re-use or disposal, as well as various control mechanisms for the medical system may be housed in the console 12. In addition to providing an exhaust function for the catheter fluid supply, the console 12 may also include pumps, valves, controllers or the like to recover and/or re-circulate fluid delivered to the handle 54, the elongate body 26, and treatment region(s) 34,44 of the medical device 14. A vacuum pump in the console 12 may create a low-pressure environment in one or more conduits within the medical device 14 so that fluid is drawn into the conduit(s) of the elongate body 26, away from the treatment region(s) 34, 44, and towards the proximal end of the elongate body 26. The console 12 may include one or more controllers, processors, and/or software modules containing instructions or algorithms to provide for the automated operation and performance of the features, sequences, or procedures described herein.

Figure 4:
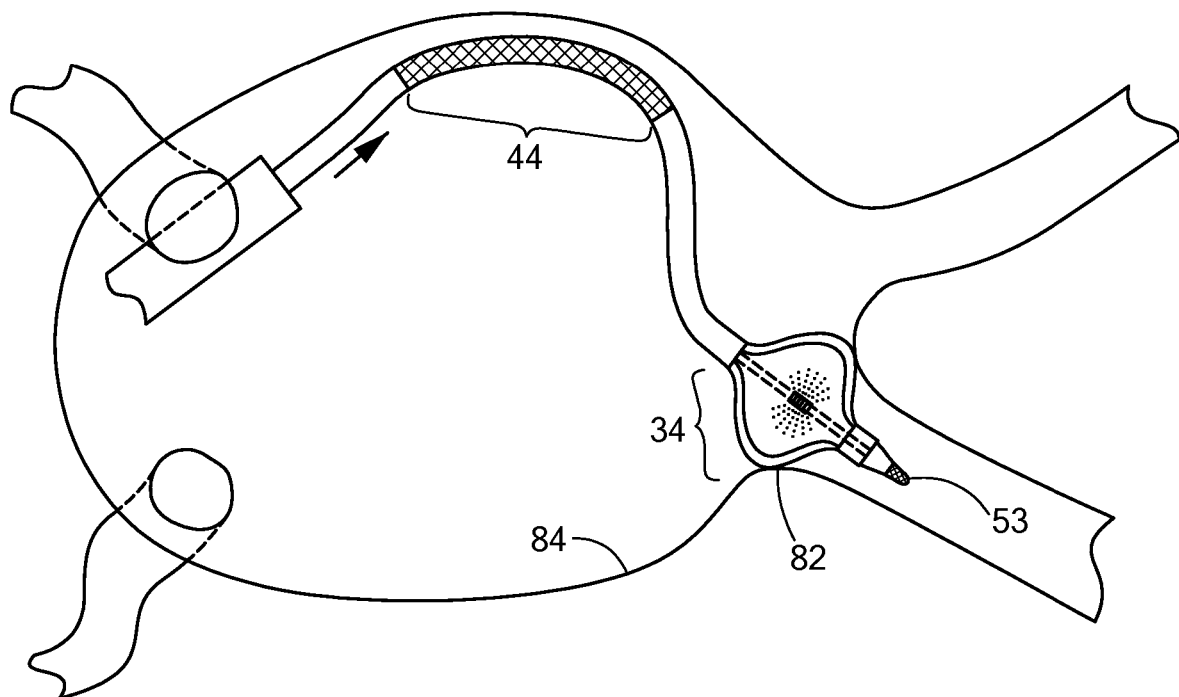
FIG. 4 is an illustration of an exemplary use of a medical device constructed in accordance with the principles of the present invention.
Figure 5:
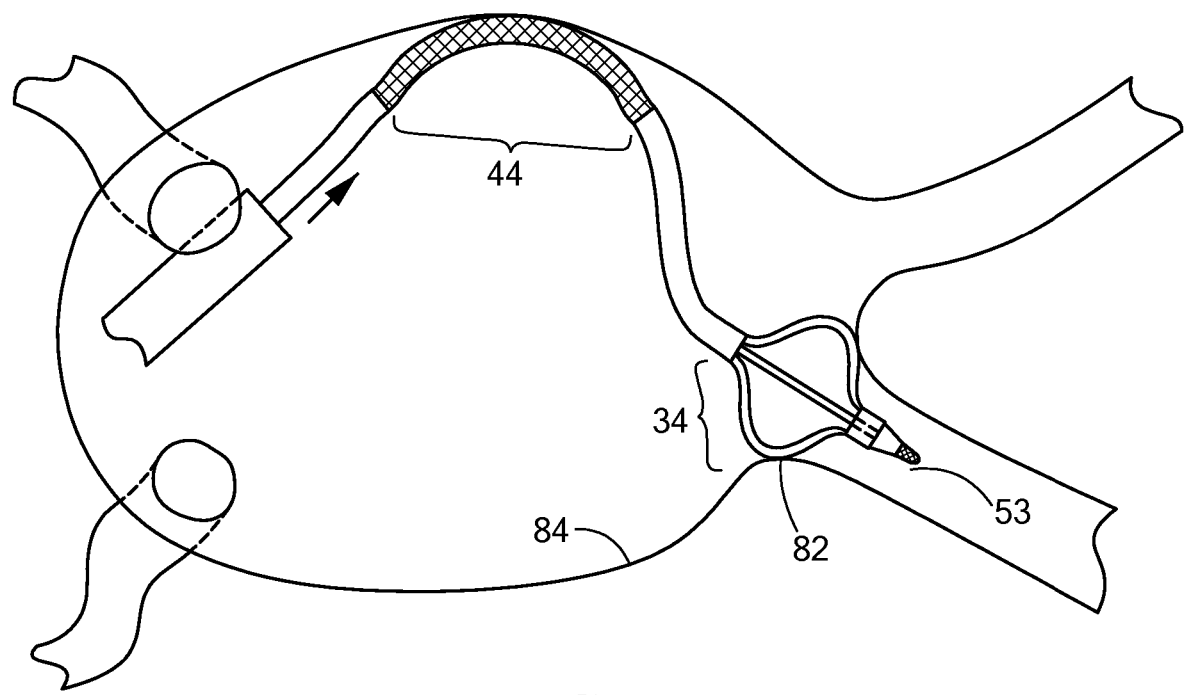
FIG. 5 is an additional illustration of an exemplary use of a medical device constructed in accordance with the principles of the present invention.

Now referring to FIGS. 4-5, in an exemplary method of use, the medical system 10 may be used to deliver therapeutic treatment to a plurality of targeted tissue areas. For example, the medical device 14 may be positioned and operated to ablate targeted tissue region in the heart. The first treatment region 34 may be positioned in the proximity of a pulmonary vein opening or junction 82 with a portion of the atrial wall 84. Where the first treatment region 34 includes an expandable element, the expandable element may be inflated or otherwise expanded to substantially occlude the pulmonary vein. The occlusion reduces the blood flow around the treatment region 34, thereby allowing enhanced thermal exchange between the medical device 14 and the targeted tissue. The occlusion may further anchor a distal portion of the medical device 14, thereby facilitating additional maneuvering, deflection, or the like of proximal portions of the catheter body 26.

In particular, once the first treatment region 34 has been positioned where desired, the second treatment region 44 may subsequently be positioned proximate targeted tissue for treatment elsewhere in the heart, such as the right atrial isthmus. The general placement and positioning of the second treatment region 44 may be facilitated by the imaging and tracking of the markers 79, 79' located at the boundaries of the second treatment region 44. Further to the general placement of the second treatment region 44, the second treatment region may then be steered or otherwise deflected towards the specific tissue to be treated. The deflection may be achieved by applying a deflection force at the proximal end of the catheter body 26, through the handle 54 for example. The force may be a compressive, linear force transmitted along a longitudinal axis of the catheter body 26. Given the anchoring of the first treatment region 34, and the increased rigidity of the catheter body segments 78, 78' adjacent the second treatment region 44, the second treatment region 44 may deflect outwards or "buckle" as a result of the linearly/longitudinally applied deflection force (as shown in FIG. 5). This deflection or "buckling" may thus cause increased contact and pressure between the second treatment region 44 and the targeted tissue, thereby providing enhanced or otherwise increased thermal exchange for tissue treatment.

Once the first and second treatment regions have be appropriately positioned as described above, the first and second treatment regions 34, 44 may be operated to affect a desired therapy, such as tissue ablation. The tissue ablation may be achieved by the circulation of a cryogenic fluid through either and/or both of the first and second treatment regions sequentially and/or simultaneously, for example.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an elongate catheter body;
   an inflatable first treatment region on the elongate catheter body having a first expandable element and a second expandable element, the first expandable element being contained within the second expandable element, the first treatment region being configured to cryoablate tissue;
   a non-expandable second treatment region distal to the first treatment region, the second treatment region being configured to deliver radiofrequency energy to ablate tissue and defining a distal tip of the medical device; and
   a non-expandable third treatment region located proximal to the first treatment region and being a proximal most treatment region, the third treatment region being configured to cryoablate tissue and being disposed between two adjacent catheter body segments.

2. The medical device of claim 1, wherein the first expandable element and the second expandable elements are balloons.

3. The medical device of claim 2, wherein the second treatment region includes a thermally conductive tip.

4. The medical device of claim 1, wherein the second treatment region is configured to be in communication with a source of radiofrequency energy.

5. The medical device of claim 1, wherein each of the first treatment region, second treatment region, and third treatment region is operable independently from the other two treatment regions.

6. The medical device of claim 5, further comprising a first fluid flow path in fluid communication with the first treatment region, and a second fluid flow path in fluid communication with the third treatment region.

7. The medical device of claim 6, wherein the first fluid flow path is fluidly isolated from the second fluid flow path.

8. The medical device of claim 1, further comprising a radiopaque marker positioned at a boundary between the third treatment region and one of the adjacent catheter body segments.

9. An ablation system, the system comprising:
   a radiofrequency energy source; and
   an intravascular catheter including:
      a handle;
      a flexible elongate body including a proximal portion coupled to the handle and a distal portion;
      an inflatable cryogenic treatment region coupled to the distal portion of the flexible elongate body having a first expandable element and a second expandable element, the first expandable element being contained within the second expandable element;
      a non-expandable thermal segment located distal to the expandable cryogenic treatment region, wherein the non-expandable thermal segment is in communication with the radiofrequency energy source; and
      a non-expandable cryogenic treatment region located proximal to the expandable cryogenic treatment region and being disposed between two adjacent catheter body segments.

10. The system of claim 9, wherein the non-expandable thermal segment is operable independently from the inflatable cryogenic treatment region and the non-expandable cryogenic treatment region.

11. The system of claim 9, further comprising a first fluid flow path in fluid communication with the inflatable cryogenic treatment region and a second fluid flow path in fluid communication with the non-expandable cryogenic treatment region.

12. The system of claim 9, wherein the radiofrequency energy source is located within an electrocardiograph box.

13. The system of claim 11, further comprising a cryogenic fluid source in fluid communication with each of the first fluid flow path and the second fluid flow path.

14. The system of claim 9, wherein the non-expandable cryogenic treatment region is positioned between two adjacent portions of the flexible elongate body, the adjacent portions having a rigidity greater than a rigidity of the non-expandable cryogenic treatment region.

* * * * *